(12) United States Patent
Whiteker

(10) Patent No.: US 6,531,555 B2
(45) Date of Patent: Mar. 11, 2003

(54) OLEFIN OLIGOMERIZATION CATALYSTS, THEIR PRODUCTION AND USE

(75) Inventor: Gregory T. Whiteker, Charleston, WV (US)

(73) Assignee: Univation Technologies, LLP, Houston, TX (US)

(*) Notice: Subject to any disclaimer, the term of this patent is extended or adjusted under 35 U.S.C. 154(b) by 217 days.

(21) Appl. No.: 09/741,453

(22) Filed: Dec. 19, 2000

(65) Prior Publication Data

US 2002/0077431 A1 Jun. 20, 2002

(51) Int. Cl.$^7$ .............................. C08F 4/52; C08F 4/64
(52) U.S. Cl. ...................... 526/161; 526/133; 526/134; 526/165; 526/352; 585/521; 585/523; 585/525; 585/527
(58) Field of Search .................. 526/161, 165, 526/352, 134, 133; 585/521, 523, 525, 527

(56) References Cited

U.S. PATENT DOCUMENTS 6,410,664 B1 * 6/2002 Bansleben et al.

FOREIGN PATENT DOCUMENTS

| EP | 0 241 560 A1 | 10/1986 |
|---|---|---|
| EP | 0 874 005 A1 | 10/1998 |
| WO | WO 98/42664 | 10/1998 |
| WO | WO 00/37512 | 6/2000 |

OTHER PUBLICATIONS

Rogers, J. S., et al. *Ethoxyboratabenzene Zirconium Complexes: Catalysts for α–Olefin Production*, J. Am. Chem. Soc. 1997, 119, 9305–9306.

Wang, et al., *Neutral Nickel(II)–Based Catalysts for Ethylene Polymerization*, Organometallics, 1998, 17, 3149–3151.

Repo et al., *Ethylenebis(salicylindeneiminato)zirconium Dichloride: Crystal Structure and Use as a Heterogeneous Catalyst in the Polymerization of Ethylene*, Macromolecules 1997, 30, 171–175.

* cited by examiner

Primary Examiner—Caixia Lu
(74) Attorney, Agent, or Firm—Jaimes Sher; Kevin M. Faulkner

(57) ABSTRACT

This invention relates to a method to oligomerize ethylene comprising combining ethylene with a catalyst system comprising an activator and one or more phenoxide group metal compounds represented by the formula:

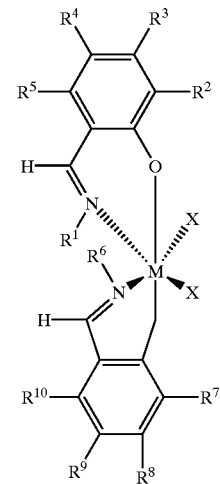

wherein $R^3$, $R^4$, $R^5$, $R^8$, $R^9$ and $R^{10}$ may each independently be hydrogen, a halogen, a heteroatom containing group or a $C_1$ to $C_{100}$ group, provided that at least one of these groups has a Hammett $\sigma_p$ value (Hansch, et al Chem. Rev. 1991, 91, 165) greater than 0.20;

$R^2$ and $R^7$ may each independently be alkyl, aryl or silyl groups;

$R^1$ and $R^6$ may each independently be an alkyl group, an aryl group, an alkoxy group, or an amino group;

N is nitrogen; H is hydrogen; O is oxygen; M is a group 4 transition metal; and each X may each independently be an anionic ligand or a dianionic ligand.

14 Claims, 3 Drawing Sheets

OLEFIN OLIGOMERIZATION CATALYSTS, THEIR PRODUCTION AND USE

FIELD OF THE INVENTION

This invention relates to a new family of olefin, in particular ethylene oligomerization catalysts based upon phenoxide complexes of transition metals and methods for their use.

BACKGROUND OF THE INVENTION

Alpha-olefins, especially those containing 4 to about 20 carbon atoms, are important items of commerce, with about 1.5 million tons reportedly being produced in 1992. The alpha-olefins are used as intermediates in the manufacture of detergents, as monomers (especially in linear low density polyethylene), and as intermediates for many other types of products. As a consequence, improved methods of making these compounds are of interest.

Most commercially produced alpha-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid such as $AlCl_3$. In all of these processes significant amounts of branched and/or internal olefins and/or diolefins, are produced. Since in most instances these are undesired, and often difficult to separate from the desired linear alpha-olefins, minimization of these byproducts is desirable.

Examples of new ethylene oligomerization catalysts which produce high purity alpha-olefins have recently appeared. Brookhart recently developed iron-based catalysts, which produce either high molecular weight HDPE or high purity α-olefins, depending on the extent of steric effects of ligand substituents. (Small, B. L.; Brookhart, M. *J. Am. Chem. Soc.* 1998, 120, 7143; U.S. Pat. No. 6,103,946.) These iron-based ethylene oligomerization catalysts exhibit very high catalytic activities and produce highly pure alpha-olefins. However, use of these catalysts to produce alpha-olefin comonomers in situ for polymerization by, for example, metallocene catalysts, could be confounded by potential incompatibilities between the iron and metallocene catalysts.

Bazan utilized electronic control of molecular weight in his studies with Zr-boratabenzene catalysts. (Rogers, J. S.; Bazan, G. C.; Sperry, C. K. *J. Am. Chem. Soc.* 1997, 119, 9305.) B-Ph boratabenzene complexes were observed to produce polyethylene, but the less electron-rich B-OMe boratabenzene analog catalyzed ethylene oligomerization. By incorporating an electron withdrawing substituent on boron, the electrophilicity of the catalyst was increased which resulted in an increased β-H elimination rate and lower molecular weight product. Like the Brookhart Fe catalyst, Bazan's boratabenzene catalyst exhibits extremely high selectivity for α-olefin production. The catalytic activity of the boratabenzene-Zr catalyst is much lower than that required for commercial operation in a tandem oligomerization/polymerization process using a metallocene polymerization catalyst.

Transition metal complexes of salicylimine ligands have recently been reported which are extremely active polymerization catalysts. Grubbs et al (Organometallics, Vol 17, 1988 page 3149–3151; WO 98/42664) disclose that nickel (II) salicylaldiminato complexes, combined with $B(C_6F_5)_3$, reacted with ethylene to form polyethylene with MW=49,500.

Ethylenebis(salicylideneiminato)zirconium dichloride combined with methyl alumoxane deposited on a support and unsupported versions were used to polymerize ethylene by Repo et al in Macromolecules 1997, 30, 171–175.

EP 241,560 A1 (Sumitomo) discloses alkoxide ligands in transition metal catalyst systems.

EP 0 874 005 A1 discloses salicylimine compounds for use as polymerization catalysts.

WO 00/37512 discloses a family of olefin polymerization catalysts based upon phenoxide complexes of transition metals.

In all of the above cases, salicylimine transition metal complexes reacted with ethylene to produce polyethylene, not ethylene oligomers or alpha-olefins. Described herein is a new class of salicylimine-based ethylene oligomerization catalysts having high activity and high selectivity for alpha-olefin. One application of these catalysts is their use in a mixed catalyst system which produces linear low density polyethylene (LLDPE) using only ethylene feedstock.

SUMMARY OF THE INVENTION

This invention relates to a process to produce alpha-olefins comprising contacting ethylene with a catalyst system comprising an activator and one or more metal catalyst compounds represented by the following formula:

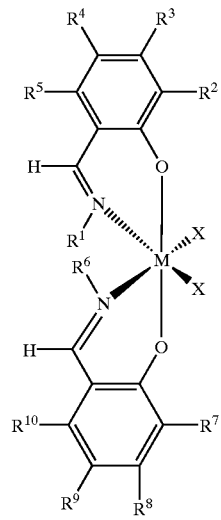

wherein
$R^3$, $R^4$, $R^5$, $R^8$, $R^9$ and $R^{10}$ may each independently be hydrogen, a halogen, a heteroatom containing group or a $C_1$ to $C_{100}$ group, provided that at least one of these groups has a Hammett $\sigma_p$ value (Hansch, et al Chem. Rev. 1991, 91, 165) greater than 0.20;

$R^2$ and $R^7$ may each independently be alkyl, aryl or silyl groups preferably tertiary alkyl, tertiary silyl or aryl groups;

$R^1$ and $R^6$ may each independently be an alkyl group, an aryl group, an alkoxy group, or an amino group, preferably a $C_1$ to $C_5$ primary alkyl group;

N is nitrogen;

H is hydrogen;

O is oxygen;

M is a group 4 transition metal; and each X may each independently be an anionic ligand such as halide, alkyl, aryl, hydride, carboxylate, alkoxide or amide, or a dianionic ligand, such as a dialkoxide or diamide.

These catalyst compounds may be activated with activators including alkyl aluminum compounds (such as diethylaluminum chloride), alumoxanes, modified alumoxanes, non-coordinating anions, non-coordinating group 13 metal or metalliod anions, boranes, borates and the like.

This invention further relates to the production of polymer by introducing ethylene, a polymerization catalyst and a catalyst system as described above into a polymerization reactor. Preferably the polymer produced is an ethylene homopolymer or an ethylene co-polymer.

DETAILED DESCRIPTION OF THE INVENTION

Figure 1:
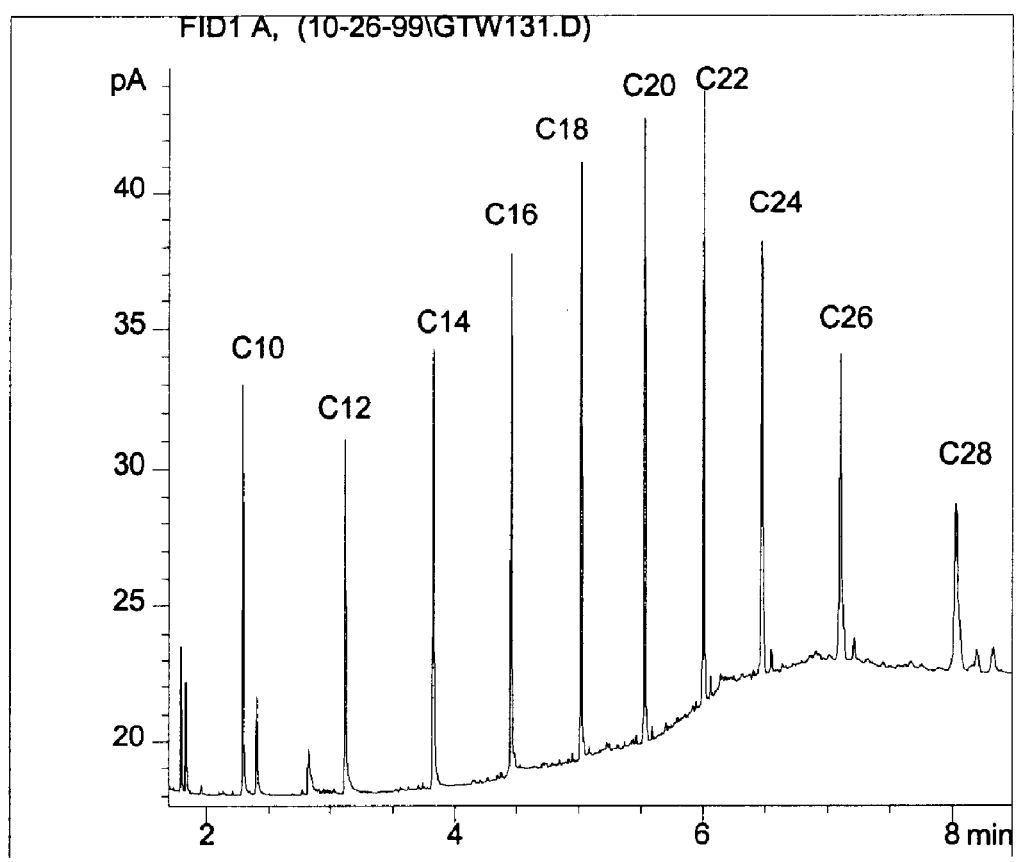
FIG. 1 is a gas chromatograph analysis of $C_{10}$–$C_{28}$ products from ethylene oligomerization by compound A in Example 1.

This invention relates to a process to produce alpha-olefins comprising contacting ethylene with a catalyst system comprising an activator and one or more metal catalyst compounds represented by the following formula:

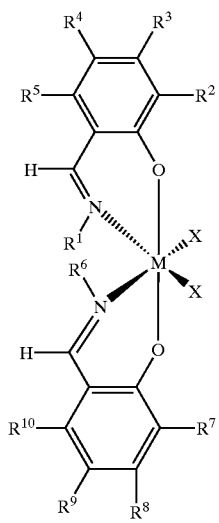

wherein $R^3$, $R^4$, $R^5$, $R^8$, $R^9$ and $R^{10}$ may each independently be hydrogen, a halogen, a heteroatom containing group or a $C_1$ to $C_{100}$ group, provided that at least one of these groups has a Hammett $\sigma_p$ value (Hansch, et al Chem. Rev. 1991, 91, 165) greater than 0.20. Specific examples of groups with $\sigma_p$>0.20 include Br, Cl, —$C_6Cl_5$, —$C_6F_5$, —$OCF_3$, —CHO, —$CF_3$ and —$NO_2$;

$R^2$ and $R^7$ may each independently be alkyl, aryl or silyl groups preferably tertiary alkyl, tertiary silyl or aryl groups, most preferably t-butyl, t-amyl, —$CMe_2Ph$, —$CMePh_2$, —$CPh_3$, —$SiMe_3$, —$SiEt_3$, —$SiMe_2tBu$, —$SiMe_2Ph$, —$SiPh_3$, α-naphthyl, phenanthrenyl or anthracenyl groups;

$R^1$ and $R^6$ may each independently be an alkyl group, an aryl group, an alkoxy group, or an amino group, preferably a $C_1$ to $C_5$ primary alkyl group, preferably methyl, ethyl, propyl or cyclopropyl or fluorinated alkyl groups, preferably —$CH_2CF_3$ or —$CH_2CF_2CF_3$;

N is nitrogen;

H is hydrogen;

O is oxygen;

M is a group 4 transition metal, preferably Ti, Zr or Hf, preferably Zr or Hf; and each X may each independently be an anionic ligand such as halide, alkyl, aryl, hydride, carboxylate, alkoxide or amide, or a dianionic ligand, such as a dialkoxide or diamide.

A heteroatom containing group may be any heteroatom or a heteroatom bound to carbon, silica or another heteroatom. Preferred heteroatoms include boron, aluminum, silicon, nitrogen, phosphorus, arsenic, tin, lead, antimony, oxygen, selenium, tellurium, bromine, chlorine, and fluorine. The heteroatom itself may be directly bound to the phenoxide ring or it may be bound to another atom or atoms that are bound to the phenoxide ring. The heteroatom containing group may contain one or more of the same or different heteroatoms. Preferred heteroatom groups include imines, amines, oxides, halides, phosphines, ethers, ketenes, oxazolines, thioethers, and the like. Particularly preferred heteroatom groups include imines. Any two adjacent R groups may form a ring structure, preferably a 5 or 6 membered ring. Likewise the R groups may form multi-ring structures.

Hammett $\sigma_p$ values for individual substituents are tabulated in the literature (Hansch, et al Chem. Rev. 1991, 91, 165). In some cases, the $\sigma_p$ value of a particular substituent may be unknown but can be experimentally determined by measurement of the $pK_a$ of the appropriate para-substituted benzoic acid in water at 25° C.

The synthesis of desired salicylimine ligands can be accomplished by reaction of salicylaldehydes with amines. Preparation of the requisite salicylaldehydes can be accomplished using standard synthetic techniques.

Metallation of the ligands can be accomplished by reaction with basic reagents such as $Zr(CH_2Ph)_4$, $Ti(NMe_2)_4$. Reaction of the ligands with $Zr(CH_2Ph)_4$ occurs with elimination of toluene, whereas reaction with $Ti(NMe_2)_4$ proceeds via amine elimination. In both cases simple alkoxide complexes are formed, as determined by $^1$H NMR spectroscopy. Alternatively, ligands can be deprotonated with reagents such as BuLi, KH or Na metal and then reacted with metal halides, such as $ZrCl_4$ or $TiCl_4$.

Specific examples of such oligomerization catalysts include the following:

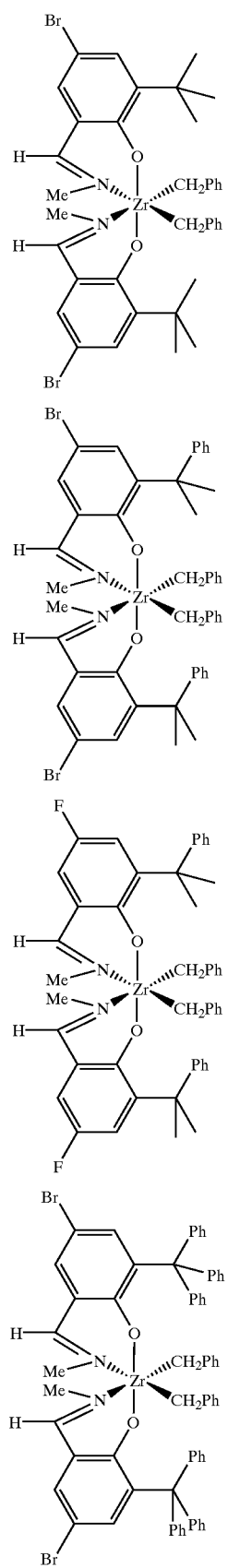
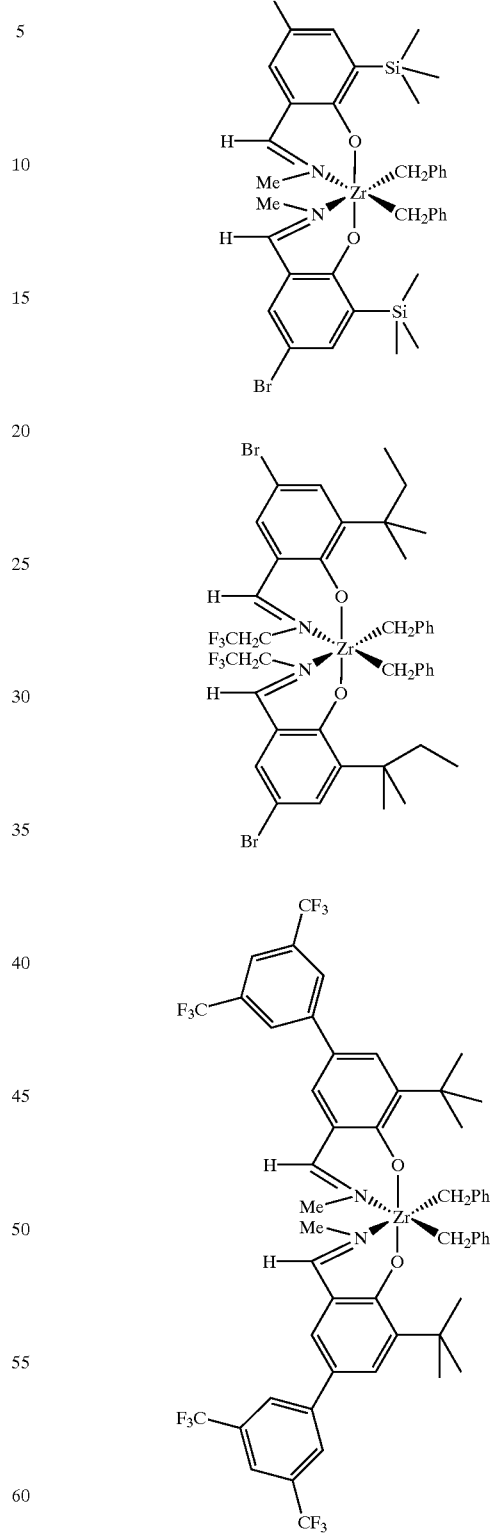

-continued

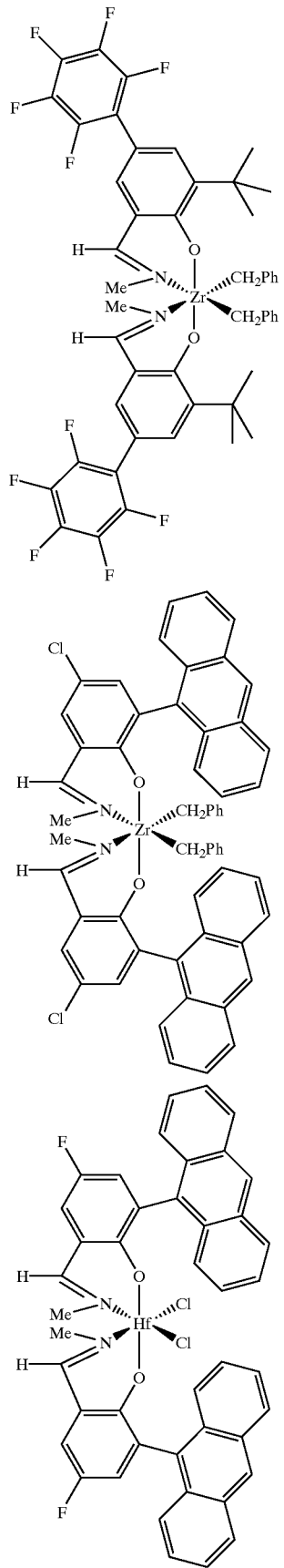

-continued

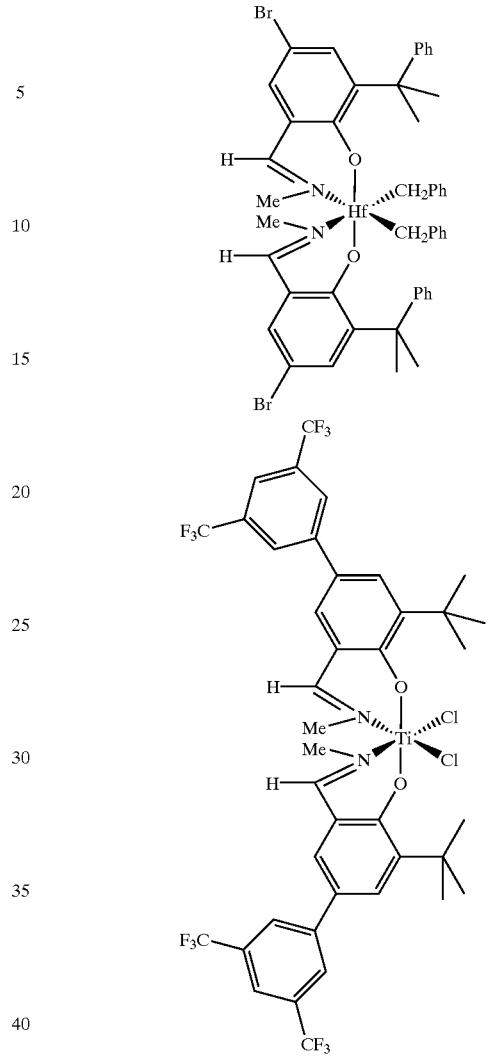

By formation of an alpha-olefin is meant formation of a compound (or mixture of compounds) of the formula $H(CH_2CH_2)_qCH=CH_2$ wherein q is an integer of 1 to about 30, preferably 1 to about 18, preferably 1 to 9. In most such reactions, the product will be a mixture of compounds having differing values of q. In most reactions to form the alpha-olefins some of the alpha-olefins formed will have q values of more than 18. Preferably less than 50 weight percent, more preferably less than 20 weight percent of the product mixture will have q values over 18. The product mixture may contain small amounts (preferably less than 30 weight percent, more preferably less than 10 weight percent, and especially preferably less than 2 weight percent) of other types of compounds such as alkanes, branched alkenes, dienes, and/or internal olefins.

Activator and Activation Methods for the Metal Catalyst Compounds

The phenoxide catalysts represented by the formula above may be activated with activators including alkyl aluminum compounds (such as diethylaluminum chloride), alumoxanes, modified alumoxanes, non-coordinating anions, non-coordinating group 13 metal or metalliod anions, boranes, borates and the like.

The above described catalyst compounds are typically activated in various ways to yield catalyst systems that will coordinate, insert, and oligomerize olefin(s). For the purposes of this patent specification and appended claims, the term "activator" is defined to be any compound or component or method which can activate any of the catalyst compounds of the invention as described above. Non-limiting activators, for example may include a Lewis acid or a non-coordinating ionic activator or ionizing activator or any other compound including Lewis bases, aluminum alkyls, conventional cocatalysts and combinations thereof. It is within the scope of this invention to use alumoxane or modified alumoxane as an activator, and/or to also use ionizing activators, neutral or ionic, such as tetra(n-butyl) ammonium tetrakis pentafluorophenyl) boron, a trisperfluorophenyl boron precursor or a trisperfluoronaphtyl boron precursor, polyhalogenated heteroborane anions (WO 98/43983), boric acid (U.S. Pat. No. 5,942,459) or combination thereof, that would ionize the neutral metallocene catalyst compound.

In one embodiment, an activation method using ionizing ionic compounds not containing an active proton but capable of producing both a catalyst cation and a non-coordinating anion are also contemplated, and are described in EP-A-0 426 637, EP-A-0 573 403 and U.S. Pat. No. 5,387,568, which are all herein incorporated by reference. An aluminum based ionizing activator is described in U.S. Pat. No. 5,602, 269 and boron and aluminum based ionizing activators are described in WO 99/06414, which are incorporated herein by reference, and are useful in this invention.

There are a variety of methods for preparing alumoxane and modified alumoxanes, non-limiting examples of which are described in U.S. Pat. Nos. 4,665,208, 4,952,540, 5,091, 352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. A preferred alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584). In other embodiments MMAO-4 and MMAO-12 may also be used.

Organoaluminum compounds useful as activators include trimethylaluminum, triethylaluminum, triisobutylaluminum, tri-n-hexylaluminum, tri-n-octylaluminum and the like.

Ionizing compounds may contain an active proton, or some other cation associated with but not coordinated to or only loosely coordinated to the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Other activators include those described in PCT publication WO 98/07515 such as tris (2,2',2"-nonafluorobiphenyl) fluoroaluminate, which publication is fully incorporated herein by reference. Combinations of activators are also contemplated by the invention, for example, alumoxanes and ionizing activators in combinations, see for example, EP-B1 0 573 120, PCT publications WO 94/07928 and WO 95/14044 and U.S. Pat. Nos. 5,153,157 and 5,453,410 all of which are herein fully incorporated by reference. WO 98/09996 incorporated herein by reference describes activating metallocene catalyst compounds with perchlorates, periodates and iodates including their hydrates. WO 98/30602 and WO 98/30603 incorporated by reference describe the use of lithium (2,2'-bisphenyl-ditrimethylsilicate)•4THF as an activator for a metallocene catalyst compound. WO 99/18135 incorporated herein by reference describes the use of organo-boron-aluminum activators. EP-B1-0 781 299 describes using a silylium salt in combination with a non-coordinating compatible anion. Also, methods of activation such as using radiation (see EP-B1-0 615 981 herein incorporated by reference), electro-chemical oxidation, and the like are also contemplated as activating methods for the purposes of rendering the neutral catalyst compound or precursor to a cation capable of oligomerizing ethylene. Other activators or methods for activating a metallocene catalyst compound are described in for example, U.S. Pat. Nos. 5,849,852, 5,859,653 and 5,869, 723 and WO 98/32775, WO 99/42467 (dioctadecylmethyl-ammonium-bis(tris(pentafluorophenyl)borane) benzimidazolide), which are herein incorporated by reference.

In general the metal compound and the activator are combined in ratios of about 1000:1 to about 0.5:1. In a preferred embodiment the metal compound and the activator are combined in a ratio of about 300:1 to about 1:1, preferably about 10:1 to about 1:1, for boranes the ratio is preferably about 1:1 to about 10:1 and for alkyl aluminum compounds (such as diethylaluminum chloride combined with water) the ratio is preferably about 0.5:1 to about 10:1.

Multiple Catalyst Systems

The phenoxide metal catalyst compounds described above may also be used in combination with one or more other metal catalyst compounds to produce polymer. The oligomerization catalyst may either be used first to produce the alpha-olefins of choice and then a polymerization catalyst is combined with the alpha olefins to produce polymer, or the oligomerization catalyst may be used at the same time as the polymerization catalyst in the same reactor to produce alpha-olefins in situ for polymerization or co-polymerization by the polymerization catalyst. For example Compound A, as described in Example 1, activator and ethylene can be introduced into a gas phase reactor to produce a mixture of alpha-olefins, while at the same time a bulky ligand metallocene catalyst compound, such as rac-dimethysilylbis (tetrahydroindenyl) zirconium dichloride, is introduced into the same reactor to copolymerize the alpha-olefins and the ethylene present. Other metal catalyst compounds that may be used in combination with the phenoxide oligomerization catalysts described above include:

a) group 15 containing metal compounds (as described below);

b) bulky ligand metallocene compounds (as described below); and c) conventional type transition metal catalysts(as described below).

For purposes of this invention cyclopentadienyl group is defined to include indenyls and fluorenyls and a catalyst system is defined to comprise at least one metal catalyst compound and at least one activator. For purposes of this invention a catalyst system includes at least one catalyst compound and at least one activator.

Group 15 Containing Metal Compound

The mixed catalyst composition of the present invention may include a Group 15 containing metal compound. The Group 15 containing compound generally includes a Group 3 to 14 metal atom, preferably a Group 3 to 7, more preferably a Group 4 to 6, and even more preferably a Group 4 metal atom, bound to at least one leaving group and also bound to at least two Group 15 atoms, at least one of which is also bound to a Group 15 or 16 atom through another group.

In one preferred embodiment, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and may optionally be bound to hydrogen, a halogen, a heteroatom or a hydrocarbyl group, or a heteroatom containing group.

In a preferred embodiment, the Group 15 containing metal compound of the present invention may be represented by the formulae:

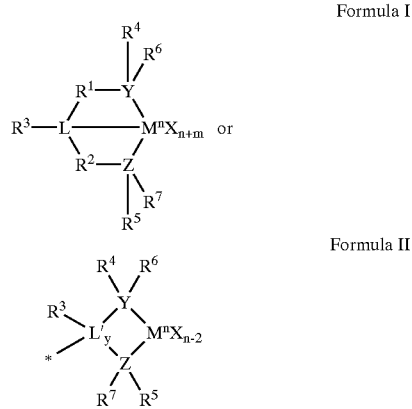

Formula I

Formula II wherein

M is a Group 3 to 12 transition metal or a Group 13 or 14 main group metal, preferably a Group 4, 5, or 6 metal, and more preferably a Group 4 metal, and most preferably zirconium, titanium or hafnium, each X is independently a leaving group, preferably, an anionic leaving group, and more preferably hydrogen, a hydrocarbyl group, a heteroatom or a halogen, and most preferably an alkyl, y is 0 or 1 (when y is 0 group L' is absent), n is the oxidation state of M, preferably +3, +4, or +5, and more preferably +4, m is the formal charge of the YZL or the YZL' ligand, preferably 0, −1, −2 or −3, and more preferably −2, L is a Group 15 or 16 element, preferably nitrogen, L' is a Group 15 or 16 element or Group 14 containing group, preferably carbon, silicon or germanium, Y is a Group 15 element, preferably nitrogen or phosphorus, and more preferably nitrogen, Z is a Group 15 element, preferably nitrogen or phosphorus, and more preferably nitrogen, $R^1$ and $R^2$ are independently a $C_1$ to $C_{20}$ hydrocarbon group, a heteroatom containing group having up to twenty carbon atoms, silicon, germanium, tin, lead, halogen or phosphorus, preferably a $C_2$ to $C_{20}$ alkyl, aryl or aralkyl group, more preferably a linear, branched or cyclic $C_2$ to $C_{20}$ alkyl group, most preferably a $C_2$ to $C_6$ hydrocarbon group. $R^1$ and $R^2$ may also be interconnected to each other, $R^3$ is absent or a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen $R^4$ and $R^5$ are independently an alkyl group, an aryl group, substituted aryl group, a cyclic alkyl group, a substituted cyclic alkyl group, a cyclic aralkyl group, a substituted cyclic aralkyl group or multiple ring system, preferably having up to 20 carbon atoms, more preferably between 3 and 10 carbon atoms, and even more preferably a $C_1$ to $C_{20}$ hydrocarbon group, a $C_1$ to $C_{20}$ aryl group or a $C_1$ to $C_{20}$ aralkyl group, or a heteroatom containing group, for example $PR_3$, where R is an alkyl group, $R^1$ and $R^2$ may be interconnected to each other, and/or $R^4$ and $R^5$ may be interconnected to each other, $R^6$ and $R^7$ are independently absent, or hydrogen, an alkyl group, halogen, heteroatom or a hydrocarbyl group, preferably a linear, cyclic or branched alkyl group having 1 to 20 carbon atoms, more preferably absent, and R* is absent, or is hydrogen, a Group 14 atom containing group, a halogen, or a heteroatom containing group.

By "formal charge of the YZL or YZL' ligand", it is meant the charge of the entire ligand absent the metal and the leaving groups X.

By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

An alkyl group may be a linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In a preferred embodiment $R^4$ and $R^5$ are independently a group represented by the following formula:

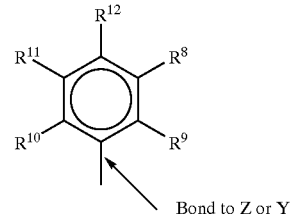

Formula 1

Bond to Z or Y wherein $R^8$ to $R^{12}$ are each independently hydrogen, a $C_1$ to $C_{40}$ alkyl group, a halide, a heteroatom, a heteroatom containing group containing up to 40 carbon atoms, preferably a $C_1$ to $C_{20}$ linear or branched alkyl group, preferably a methyl, ethyl, propyl or butyl group, any two R groups may form a cyclic group and/or a heterocyclic group. The cyclic groups may be aromatic. In a preferred embodiment $R^9$, $R^{10}$ and $R^{12}$ are independently a methyl, ethyl, propyl or butyl group (including all isomers), in a preferred embodiment $R^9$, $R^{10}$ and $R^{12}$ are methyl groups, and $R^8$ and $R^{11}$ are hydrogen.

In a particularly preferred embodiment $R^4$ and $R^5$ are both a group represented by the following formula:

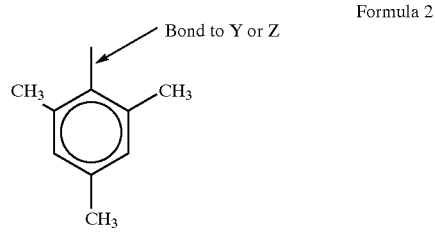

Formula 2

In this embodiment, M is a Group 4 metal, preferably zirconium, titanium or hafnium, and even more preferably zirconium; each of L, Y, and Z is nitrogen; each of $R^1$ and $R^2$ is —$CH_2$—$CH_2$—; $R^3$ is hydrogen; and $R^6$ and $R^7$ are absent.

In a particularly preferred embodiment the Group 15 containing metal compound is represented by the formula:

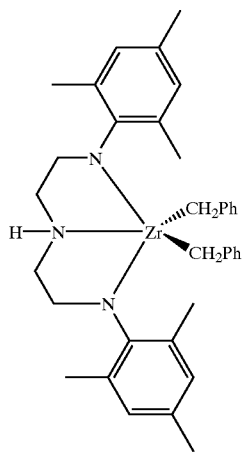

Compound I

In compound I, Ph equals phenyl.

The Group 15 containing metal compounds of the invention are prepared by methods known in the art, such as those disclosed in EP 0 893 454 A1, U.S. Pat. No. 5,889,128 and the references cited in U.S. Pat. No. 5,889,128 which are all herein incorporated by reference. U.S. application Ser. No. 09/312,878, filed May 17, 1999, discloses a gas or slurry phase polymerization process using a supported bisamide catalyst, which is also incorporated herein by reference.

A preferred direct synthesis of these compounds comprises reacting the neutral ligand, (see for example YZL or YZL' of formula 1 or 2) with $M^nX_n$ (M is a Group 3 to 14 metal, n is the oxidation state of M, each X is an anionic group, such as halide, in a non-coordinating or weakly coordinating solvent, such as ether, toluene, xylene, benzene, methylene chloride, and/or hexane or other solvent having a boiling point above 60° C., at about 20 to about 150° C. (preferably 20 to 100° C.), preferably for 24 hours or more, then treating the mixture with an excess (such as four or more equivalents) of an alkylating agent, such as methyl magnesium bromide in ether. The magnesium salts are removed by filtration, and the metal complex isolated by standard techniques.

In one embodiment the Group 15 containing metal compound is prepared by a method comprising reacting a neutral ligand, (see for example YZL or YZL' of formula 1 or 2) with a compound represented by the formula $M^nX_n$ (where M is a Group 3 to 14 metal, n is the oxidation state of M, each X is an anionic leaving group) in a non-coordinating or weakly coordinating solvent, at about 20° C. or above, preferably at about 20 to about 100° C., then treating the mixture with an excess of an alkylating agent, then recovering the metal complex. In a preferred embodiment the solvent has a boiling point above 60° C., such as toluene, xylene, benzene, and/or hexane. In another embodiment the solvent comprises ether and/or methylene chloride, either being preferable.

For additional information of Group 15 containing metal compounds, please see Mitsui Chemicals, Inc. in EP 0 893 454 A1 which discloses transition metal amides combined with activators to polymerize olefins.

The Group 15 containing metal compounds are typically combined with an activator to form a catalyst system and then used to polymerize olefins. The activators may be any of the activators named in the section above entitled "Activator and Activation Methods for the Metal Catalyst Compounds."

Bulky Ligand Metallocene Compounds

Bulky ligand metallocene compounds (hereinafter also referred to as metallocenes) may also be used in the practice of this invention.

Generally, bulky ligand metallocene compounds include half and full sandwich compounds having one or more bulky ligands bonded to at least one metal atom. Typical bulky ligand metallocene compounds are generally described as containing one or more bulky ligand(s) and one or more leaving group(s) bonded to at least one metal atom. In one preferred embodiment, at least one bulky ligand is η-bonded to the metal atom, most preferably $\eta^5$-bonded to the metal atom.

The bulky ligands are generally represented by one or more open, acyclic, or fused ring(s) or ring system(s) or a combination thereof. These bulky ligands, preferably the ring(s) or ring system(s) are typically composed of atoms selected from Groups 13 to 16 atoms of the Periodic Table of Elements, preferably the atoms are selected from the group consisting of carbon, nitrogen, oxygen, silicon, sulfur, phosphorous, germanium, boron and aluminum or a combination thereof. Most preferably the ring(s) or ring system(s) are composed of carbon atoms such as but not limited to those cyclopentadienyl ligands or cyclopentadienyl-type ligand structures or other similar functioning ligand structure such as a pentadiene, a cyclooctatetraendiyl or an imide ligand. The metal atom is preferably selected from Groups 3 through 15 and the lanthanide or actinide series of the Periodic Table of Elements. Preferably the metal is a transition metal from Groups 4 through 12, more preferably Groups 4, 5 and 6, and most preferably the transition metal is from Group 4.

In one embodiment, the bulky ligand metallocene catalyst compounds are represented by the formula:

$$L^A L^B MQ_n \qquad (III)$$

where M is a metal atom from the Periodic Table of the Elements and may be a Group 3 to 12 metal or from the lanthanide or actinide series of the Periodic Table of Elements, preferably M is a Group 4, 5 or 6 transition metal, more preferably M is a Group 4 transition metal, even more preferably M is zirconium, hafnium or titanium. The bulky ligands, $L^A$ and $L^B$, are open, acyclic or fused ring(s) or ring system(s) and are any ancillary ligand system, including unsubstituted or substituted, cyclopentadienyl ligands or cyclopentadienyl-type ligands, heteroatom substituted and/or heteroatom containing cyclopentadienyl-type ligands. Non-limiting examples of bulky ligands include cyclopentadienyl ligands, cyclopentaphenanthreneyl ligands, indenyl ligands, benzindenyl ligands, fluorenyl ligands, octahydrofluorenyl ligands, cyclooctatetraendiyl ligands, cyclopentacyclododecene ligands, azenyl ligands, azulene ligands, pentalene ligands, phosphoyl ligands, phosphinimine (WO 99/40125), pyrrolyl ligands, pyrozolyl ligands, carbazolyl ligands, borabenzene ligands and the like, including hydrogenated versions thereof, for example tetrahydroindenyl ligands. In one embodiment, $L^A$ and $L^B$ may be any other ligand structure capable of η-bonding to M, preferably $η^3$-bonding to M and most preferably $η^5$-bonding. In yet another embodiment, the atomic molecular weight (MW) of $L^A$ or $L^B$ exceeds 60 a.m.u., preferably greater than 65 a.m.u.. In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a heterocyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazomacrocycles. Independently, each $L^A$ and $L^B$ may be the same or different type of bulky ligand that is bonded to M. In one embodiment of formula (III) only one of either $L^A$ or $L^B$ is present.

Independently, each $L^A$ and $L^B$ may be unsubstituted or substituted with a combination of substituent groups R. Non-limiting examples of substituent groups R include one or more from the group selected from hydrogen, or linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. In a preferred embodiment, substituent groups R have up to 50 non-hydrogen atoms, preferably from 1 to 30 carbon, that can also be substituted with halogens or heteroatoms or the like. Non-limiting examples of alkyl substituents R include methyl, ethyl, propyl, butyl, pentyl, hexyl, cyclopentyl, cyclohexyl, benzyl or phenyl groups and the like, including all their isomers, for example tertiary butyl, isopropyl, and the like. Other hydrocarbyl radicals include fluoromethyl, fluroethyl, difluroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)-silyl, methyl-bis(difluoromethyl)silyl, bromomethyldimethylgermyl and the like; and disubstitiuted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorous, oxygen, tin, sulfur, germanium and the like, including olefins such as but not limited to olefinically unsaturated substituents including vinyl-terminated ligands, for example but-3-enyl, prop-2-enyl, hex-5-enyl and the like. Also, at least two R groups, preferably two adjacent R groups, are joined to form a ring structure having from 3 to 30 atoms selected from carbon, nitrogen, oxygen, phosphorous, silicon, germanium, aluminum, boron or a combination thereof. Also, a substituent group R group such as 1-butanyl may form a carbon sigma bond to the metal M.

Other ligands may be bonded to the metal M, such as at least one leaving group Q. In one embodiment, Q is a monoanionic labile ligand having a sigma-bond to M. Depending on the oxidation state of the metal, the value for n is 0, 1 or 2 such that formula (III) above represents a neutral bulky ligand metallocene-type catalyst compound.

Non-limiting examples of Q ligands include weak bases such as amines, phosphines, ethers, carboxylates, dienes, hydrocarbyl radicals having from 1 to 20 carbon atoms, hydrides or halogens and the like or a combination thereof. In another embodiment, two or more Q's form a part of a fused ring or ring system. Other examples of Q ligands include those substituents for R as described above and including cyclobutyl, cyclohexyl, heptyl, tolyl, trifluromethyl, tetramethylene, pentamethylene, methylidene, methyoxy, ethyoxy, propoxy, phenoxy, bis(N-methylanilide), dimethylamide, dimethylphosphide radicals and the like.

The two L groups may be bridged together by group A as defined below.

In one embodiment, the bulky ligand metallocene-type catalyst compounds of the invention include those of formula (III) where $L^A$ and $L^B$ are bridged to each other by at least one bridging group, A, such that the formula is represented by $$L^A A L^B M Q_n \qquad (IV)$$

These bridged compounds represented by formula (IV) are known as bridged, bulky ligand metallocene-type catalyst compounds. $L^A$, $L^B$, M, Q and n are as defined above. Non-limiting examples of bridging group A include bridging groups containing at least one Group 13 to 16 atom, often referred to as a divalent moiety such as but not limited to at least one of a carbon, oxygen, nitrogen, silicon, aluminum, boron, germanium and tin atom or a combination thereof. Preferably bridging group A contains a carbon, silicon or germanium atom, most preferably A contains at least one silicon atom or at least one carbon atom. The bridging group A may also contain substituent groups R as defined above including halogens and iron. Non-limiting examples of bridging group A may be represented by $R'_2C$, $R'_2Si$, $R'_2Si$ $R'_2Si$, $R'_2Ge$, R'P, where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system. In one embodiment, the bridged, bulky ligand metallocene-type catalyst compounds of formula (IV) have two or more bridging groups A (EP 664 301 B1).

In one embodiment, the bulky ligand metallocene-type catalyst compounds are those where the R substituents on the bulky ligands $L^A$ and $L^B$ of formulas (III) and (IV) are substituted with the same or different number of substituents on each of the bulky ligands. In another embodiment, the bulky ligands $L^A$ and $L^B$ of formulas (III) and (IV) are different from each other.

Other bulky ligand metallocene catalyst compounds and catalyst systems useful in the invention may include those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517 and 5,939,503 and PCT publications WO 93/08221, WO 93/08199, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-B1-0 632 819, EP-B1-0 748 821 and EP-B1-0 757 996, all of which are herein fully incorporated by reference.

In one embodiment, bulky ligand metallocene-type catalysts compounds useful in the invention include bridged heteroatom, mono-bulky ligand metallocene-type compounds. These types of catalysts and catalyst systems are described in, for example, PCT publication WO 92/00333, WO 94/07928, WO 91/04257, WO 94/03506, WO96/00244, WO 97/15602 and WO 99/20637 and U.S. Pat. Nos. 5,057, 475, 5,096,867, 5,055,438, 5,198,401, 5,227,440 and 5,264, 405 and European publication EP-A-0 420 436, all of which are herein fully incorporated by reference.

In this embodiment, the bulky ligand metallocene catalyst compound is represented by the formula:

$$L^C A J M Q_n \qquad (V)$$

where M is a Group 3 to 16 metal atom or a metal selected from the Group of actinides and lanthanides of the Periodic Table of Elements, preferably M is a Group 4 to 12 transition metal, and more preferably M is a Group 4, 5 or 6 transition metal, and most preferably M is a Group 4 transition metal in any oxidation state, especially titanium; $L^C$ is a substituted or unsubstituted bulky ligand bonded to M; J is bonded to M; A is bonded to M and J; J is a heteroatom ancillary ligand; and A is a bridging group bound to $L^C$ and J; Q is a univalent anionic ligand; and n is the integer 0,1 or 2. In formula (V) above, $L^C$, A and J form a fused ring system. In an embodiment, $L^C$ of formula (V) is as defined above for $L^A$, A, M and Q of formula (V) are as defined above in formula (III).

In formula (V) J is a heteroatom containing ligand in which J is an element with a coordination number of three from Group 15 or an element with a coordination number of two from Group 16 of the Periodic Table of Elements. Preferably J contains a nitrogen, phosphorus, oxygen or sulfur atom with nitrogen being most preferred.

In an embodiment of the invention, the bulky ligand metallocene catalyst compounds are heterocyclic ligand complexes where the bulky ligands, the ring(s) or ring system(s), include one or more heteroatoms or a combination thereof. Non-limiting examples of heteroatoms include a Group 13 to 16 element, preferably nitrogen, boron, sulfur, oxygen, aluminum, silicon, phosphorous and tin. Examples of these bulky ligand metallocene-type catalyst compounds are described in WO 96/33202, WO 96/34021, WO 97/17379 and WO 98/22486 and EP-A1-0 874 005 and U.S. Pat. Nos. 5,637,660, 5,539,124, 5,554,775, 5,756,611, 5,233,049, 5,744,417, and 5,856,258 all of which are herein incorporated by reference.

In one embodiment, the bulky ligand metallocene catalyst compounds are those complexes known as transition metal catalysts based on bidentate ligands containing pyridine or quinoline moieties, such as those described in U.S. application Ser. No. 09/103,620 filed Jun. 23, 1998, which is herein incorporated by reference. In another embodiment, the bulky ligand metallocene catalyst compounds are those described in PCT publications WO 99/01481 and WO 98/42664, which are fully incorporated herein by reference.

In a preferred embodiment, the bulky ligand metallocene catalyst compound is a complex of a metal, preferably a transition metal, a bulky ligand, preferably a substituted or unsubstituted pi-bonded ligand, and one or more heteroallyl moieties, such as those described in U.S. Pat. Nos. 5,527,752 and 5,747,406 and EP-B 1-0 735 057, all of which are herein fully incorporated by reference.

In a particularly preferred embodiment, the other metal compound or second metal compound is the bulky ligand metallocene catalyst compound is represented by the formula:

$$L^D MQ_2(YZ)X_n \qquad (VI)$$

where M is a Group 3 to 16 metal, preferably a Group 4 to 12 transition metal, and most preferably a Group 4, 5 or 6 transition metal; $L^D$ is a bulky ligand that is bonded to M; each Q is independently bonded to M and $Q_2$(YZ) forms a ligand, preferably a unicharged polydentate ligand; A or Q is a univalent anionic ligand also bonded to M; X is a univalent anionic group when n is 2 or X is a divalent anionic group when n is 1; n is 1 or 2.

In formula (VI), L and M are as defined above for formula (III). Q is as defined above for formula (III), preferably Q is selected from the group consisting of —O—, —NR—, —CR$_2$— and —S—; Y is either C or S; Z is selected from the group consisting of —OR, —NR$_2$, —CR$_3$, —SR, —SiR$_3$, —PR$_2$, —H, and substituted or unsubstituted aryl groups, with the proviso that when Q is —NR— then Z is selected from one of the group consisting of —OR, —NR$_2$, —SR, —SiR$_3$, —PR$_2$ and —H; R is selected from a group containing carbon, silicon, nitrogen, oxygen, and/or phosphorus, preferably where R is a hydrocarbon group containing from 1 to 20 carbon atoms, most preferably an alkyl, cycloalkyl, or an aryl group; n is an integer from 1 to 4, preferably 1 or 2; X is a univalent anionic group when n is 2 or X is a divalent anionic group when n is 1; preferably X is a carbamate, carboxylate, or other heteroallyl moiety described by the Q, Y and Z combination.

Conventional-Type Transition Metal Catalysts

In another embodiment, conventional-type transition metal catalysts may be used in the practice of this invention. Conventional-type transition metal catalysts are those traditional Ziegler-Natta, vanadium and Phillips-type catalysts well known in the art. Such as, for example Ziegler-Natta catalysts as described in *Ziegler-Natta Catalysts and Polymerizations,* John Boor, Academic Press, New York, 1979. Examples of conventional-type transition metal catalysts are also discussed in U.S. Pat. Nos. 4,115,639, 4,077, 904, 4,482,687, 4,564,605, 4,721,763, 4,879,359 and 4,960, 741 all of which are herein fully incorporated by reference. The conventional-type transition metal catalyst compounds that may be used in the present invention include transition metal compounds from Groups 3 to 17, preferably 4 to 12, more preferably 4 to 6 of the Periodic Table of Elements.

Preferred conventional-type transition metal catalysts may be represented by the formula: MR$_x$, where M is a metal from Groups 3 to 17, preferably Group 4 to 6, more preferably Group 4, most preferably titanium; R is a halogen or a hydrocarbyloxy group; and x is the oxidation state of the metal M. Non-limiting examples of R include alkoxy, phenoxy, bromide, chloride and fluoride. Non-limiting examples of conventional-type transition metal catalysts where M is titanium include TiCl$_4$, TiBr$_4$, Ti(OC$_2$H$_5$)$_3$Cl, Ti(OC$_2$H$_5$)Cl$_3$, Ti(OC$_4$H$_9$)$_3$Cl, 3Ti(OC$_3$H$_7$)$_2$Cl$_2$, Ti(OC$_2$H$_5$)$_2$Br$_2$, TiCl$_3$.1/3AlCl$_3$ and Ti(OC$_{12}$H$_{25}$)Cl$_3$.

Conventional-type transition metal catalyst compounds based on magnesium/titanium electron-donor complexes that are useful in the invention are described in, for example, U.S. Pat. Nos. 4,302,565 and 4,302,566, which are herein fully incorporate by reference. The MgTiCl$_6$ (ethyl acetate)$_4$ derivative is particularly preferred.

British Patent Application 2,105,355 and U.S. Pat. No. 5,317,036, herein incorporated by reference, describes various conventional-type vanadium catalyst compounds. Non-limiting examples of conventional-type vanadium catalyst compounds include vanadyl trihalide, alkoxy halides and alkoxides such as VOCl$_3$, VOCl$_2$(OBu) where Bu=butyl and VO(OC$_2$H$_5$)$_3$; vanadium tetra-halide and vanadium alkoxy halides such as VCl$_4$ and VCl$_3$(OBu); vanadium and vanadyl acetyl acetonates and chloroacetyl acetonates such as V(AcAc)$_3$ and VOCl$_2$(AcAc) where (AcAc) is an acetyl acetonate. The preferred conventional-type vanadium catalyst compounds are VOCl$_3$, VCl$_4$ and VOCl$_2$—OR where R is a hydrocarbon radical, preferably a C$_1$ to C$_{10}$ aliphatic or aromatic hydrocarbon radical such as ethyl, phenyl, isopropyl, butyl, propyl, n-butyl, iso-butyl, tertiary-butyl, hexyl, cyclohexyl, naphthyl, etc., and vanadium acetyl acetonates.

Conventional-type chromium catalyst compounds, often referred to as Phillips-type catalysts, suitable for use in the present invention include CrO$_3$, chromocene, silyl chromate, chromyl chloride (CrO$_2$Cl$_2$), chromium-2-ethyl-hexanoate, chromium acetylacetonate (Cr(AcAc)$_3$), and the like. Non-limiting examples are disclosed in U.S. Pat. Nos. 3,709,853, 3,709,954, 3,231,550, 3,242,099 and 4,077,904, which are herein fully incorporated by reference.

Still other conventional-type transition metal catalyst compounds and catalyst systems suitable for use in the present invention are disclosed in U.S. Pat. Nos. 4,124,532, 4,302,565, 4,302,566, 4,376,062, 4,379,758, 5,066,737, 5,763,723, 5,849,655, 5,852,144, 5,854,164 and 5,869,585 and published EP-A2 0 416 815 A2 and EP-A1 0 420 436, which are all herein incorporated by reference.

Other catalysts may include cationic catalysts such as AlCl$_3$, and other cobalt, iron, nickel and palladium catalysts well known in the art. See for example U.S. Pat. Nos. 3,487,112, 4,472,559, 4,182,814 and 4,689,437 all of which are incorporated herein by reference.

Typically, these conventional-type transition metal catalyst compounds excluding some conventional-type chromium catalyst compounds are activated with one or more of the conventional-type cocatalysts described below.

Conventional-Type Cocatalysts

Conventional-type cocatalyst compounds for the above conventional-type transition metal catalyst compounds may be represented by the formula M$^3$M$^4$$_v$X$^2$$_c$R$^3$$_{b-c}$, wherein M$^3$ is a metal from Group 1 to 3 and 12 to 13 of the Periodic Table of Elements; M$^4$ is a metal of Group 1 of the Periodic Table of Elements; v is a number from 0 to 1; each X$^2$ is any halogen; c is a number from 0 to 3; each R$^3$ is a monovalent hydrocarbon radical or hydrogen; b is a number from 1 to 4; and wherein b minus c is at least 1. Other conventional-type organometallic cocatalyst compounds for the above conventional-type transition metal catalysts have the formula M$^3$R$^3$$_k$, where M$^3$ is a Group IA, IIA, IIB or IIIA metal, such as lithium, sodium, beryllium, barium, boron, aluminum, zinc, cadmium, and gallium; k equals 1, 2 or 3 depending upon the valency of M$^3$ which valency in turn normally depends upon the particular Group to which M$^3$ belongs; and each R$^3$ may be any monovalent hydrocarbon radical.

Non-limiting examples of conventional-type organometallic cocatalyst compounds useful with the conventional-type catalyst compounds described above include methyllithium, butyllithium, dihexylmercury, butylmagnesium, diethylcadmium, benzylpotassium, diethylzinc, tri-n-butylaluminum, diisobutyl ethylboron, diethylcadmium, di-n-butylzinc and tri-n-amylboron, and, in particular, the aluminum alkyls, such as tri-hexyl-aluminum, triethylaluminum, trimethylaluminum, and tri-isobutylaluminum. Other conventional-type cocatalyst compounds include mono-organohalides and hydrides of Group 2 metals, and mono- or di-organohalides and hydrides of Group 3 and 13 metals. Non-limiting examples of such conventional-type cocatalyst compounds include di-isobutylaluminum bromide, isobutylboron dichloride, methyl magnesium chloride, ethylberyllium chloride, ethylcalcium bromide, di-isobutylaluminum hydride, methylcadmium hydride, diethylboron hydride, hexylberyllium hydride, dipropylboron hydride, octylmagnesium hydride, butylzinc hydride, dichloroboron hydride, di-bromo-aluminum hydride and bromocadmium hydride. Conventional-type organometallic cocatalyst compounds are known to those in the art and a more complete discussion of these compounds may be found in U.S. Pat. Nos. 3,221,002 and 5,093,415, which are herein fully incorporated by reference.

Supports, Carriers and General Supporting Techniques

The above described catalyst compounds, activators and/or catalyst systems may be combined with one or more support materials or carriers.

For example, in a most preferred embodiment, the activator is contacted with a support to form a supported activator wherein the activator is deposited on, contacted with, vaporized with, bonded to, or incorporated within, adsorbed or absorbed in, or on, a support or carrier.

Support materials of the invention include inorganic or organic support materials, preferably a porous support material. Non-limiting examples of inorganic support materials include inorganic oxides and inorganic chlorides. Other carriers include resinous support materials such as polystyrene, functionalized or crosslinked organic supports, such as polystyrene divinyl benzene, polyolefins or polymeric compounds, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina (WO 99/60033), silica-alumina and mixtures thereof Other useful supports include magnesia, titania, zirconia, magnesium chloride (U.S. Pat. No. 5,965,477), montmorillonite (EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B 1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. A preferred support is fumed silica available under the trade name Cabosil™ TS-610, available from Cabot Corporation. Fumed silica is typically a silica with particles 7 to 30 nanometers in size that has been treated with dimethylsilyldichloride such that a majority of hydroxyl groups are capped.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 μm. More preferably, the surface area of the support is in the range of from about 50 to about 500 m$^2$/g, pore volume of from about 0.5 to about 3.5 cc/g and average particle size of from about 10 to about 200 μm. Most preferably the surface area of the support is in the range from about 100 to about 1000 m$^2$/g, pore volume from about 0.8 to about 5.0 cc/g and average particle size is from about 5 to about 100 μm. The average pore size of the support material of the invention typically has pore size in the range of from 10 to 1000 Å, preferably 50 to about 500 Å, and most preferably 75 to about 450 Å.

Oligomerization

The catalysts and catalyst systems described above can be used in any known olefin oligomerization process including gas phase, solution, slurry and high pressure. The catalysts and catalyst systems described above are particularly suitable for use in a solution or slurry oligomerization process or a combination thereof.

In one embodiment, this invention is directed toward the solution, slurry phase, high pressure or gas phase oligomerization reactions involving the oligomerization of ethylene.

In the preferred oligomerization processes herein, the temperature at which it is carried out is about −100° C. to about +300° C., preferably about 0° C. to about 200° C., more preferably about 50° C. to about 150° C. It is preferred to carry out the oligomerization under ethylene (gauge) pressures from about 0 kPa to about 35 MPa, more preferably about 500 kPa to about 15 MPa. It is preferred that the oligomerization be carried under conditions at which the reaction is not significantly diffusion limited.

Generally speaking, the alpha-olefin production (also called oligomerization) processes herein may be run in the presence of various liquids, particularly aprotic organic liquids. The catalyst system, and alpha-olefin product may be soluble or insoluble in these liquids, but preferably these liquids should not prevent the oligomerization from occurring. Suitable liquids include alkanes, alkenes cycloalkanes, selected halogenated hydrocarbons, and aromatic hydrocarbons. Specific useful solvents include hexane, toluene, the alpha-olefins themselves, and benzene.

The formation of the alpha-olefins as described herein is relatively rapid in many instances, and significant yields can be obtained in less than an hour. Likewise very high selectivity for alpha-olefins can also be obtained.

Also under certain conditions, mixtures of alpha-olefins containing desirable numbers of carbon atoms are obtained. A measure of the molecular weights of the olefins obtained is factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276). This is defined as: K=n($C_{n+2}$ olefin)/n($C_n$ olefin) wherein n($C_n$ olefin) is the number of moles of olefin containing n carbon atoms, and n($C_{n+2}$ olefin) is the number of moles of olefin containing n+2 carbon atoms, or in other words the next higher ethylene oligomer. From this can be determined the weight (mass) fractions of the various olefins in the resulting oligomeric reaction product mixture. The K factor is preferred to be in the range of about 0.4 to about 0.8 to make the alpha-olefins of the most commercial interest. It is also desirable to be able to vary this factor, so as to produce those olefins which are in demand at the moment.

The alpha-olefins made herein may be converted to alcohols by known processes, these alcohols being useful for a variety of applications such as intermediates for detergents or plasticizers. The alpha-olefins may be converted to alcohols by a variety of processes, such as the oxo process followed by hydrogenation, or by a modified single step oxo process, see for instance B. Elvers, et al., Ed., Ullmann's Encyclopedia of Chemical Technology, 5$^{th}$ Ed., Vol. A18, VCH Verlagsgesellschaft mbH, Weinheim, 1991, p. 321–327, which is hereby incorporated by reference.

The ethylene oligomerizations herein may also initially be carried out in the solid state by, for instance, supporting a catalyst system or catalyst compound on a substrate such as silica or alumina. Similarly, a solution of a catalyst compound may be exposed to a support having an alkylaluminum compound on its surface. The support may also be able to take the place of the Lewis or Bronsted acid, for instance an acidic clay such as montmorillonite. Another method of making a supported catalyst is to start a polymerization or at least make a metal complex of another olefin or oligomer of an olefin such as cyclopentene on a support such as silica or alumina. All of these "heterogeneous" catalysts may be used to catalyze oligomerization in the gas phase or the liquid phase. By gas phase is meant that the ethylene is transported to contact with the catalyst particle while the ethylene is in the gas phase.

In another embodiment the oligomeric mixture produced is at least 70% pure, preferably at least 80% pure, more preferably 90% pure, even more preferably at least 95% pure, more preferably at least 99% pure.

In another embodiment the oligomer products have at least 80% vinyl termination, preferably ate last 90% vinyl termination, more preferably at least 95% vinyl termination, more preferably at least 99% vinyl termination, as measured by $^1$H NMR or gas chromatography.

Polymerization

The alpha-olefins made herein may be further polymerized with other olefins to form polyolefins, especially linear low density polyethylenes, which are copolymers containing ethylene. They may also be homopolymerized. These polymers may be made by a number of known methods, such as Ziegler-Natta-type polymerization, metallocene catalyzed polymerization, and other methods, see for instance WO 96/23010, see for instance Angew. Chem., Int. Ed. Engl., vol. 34, p. 1143–1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, p. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylenes, and all of these are hereby incorporated by reference.

In another embodiment, this invention is directed toward solution, slurry or gas phase polymerization reactions involving the oligomerization/polymerization of ethylene using the described oligomerization catalyst in conjunction with one or more olefin polymerization catalyst, for example a metallocene catalyst. Additional monomers having from 3 to 30 carbon atoms, preferably 3–12 carbon atoms, and more preferably 3 to 8 carbon atoms may be additionally fed to the process. Preferred additional monomers include one or more of, propylene, butene-1, pentene-1, 4-methyl-pentene-1, 3,5, 5,-trimethyl-hexene-1, hexene-1, octene-1, decene-1, 3-methyl-pentene-1, and cyclic olefins or a combination thereof. Other monomers can include vinyl monomers, diolefins such as dienes, polyenes, norbornene, norbornadiene monomers. In one embodiment, a linear low density polyethylene (LLDPE) is produced from ethylene without external addition of alpha-olefin comonomer.

The metal catalyst compounds of the present invention may be combined with another, different metal catalyst compound to produce a polymer product that preferably has both high molecular weight components and low molecular weight components. For simplicity, the combined catalyst system will be described as polymerizing the monomer, even though a more accurate description might be that one of the catalyst metal compounds is oligomerizing at the same time that the other catalyst compound is polymerizing.

In one embodiment of the invention, an oligomerization metal catalyst compound described above is combined with a polymerization catalyst metal compound and at least one activator and thereafter contacted with olefins under reaction condition in a gas phase, slurry phase or solution phase process as described below to produce a polymer product.

When two different metal catalyst compounds are used, the first and second catalyst compounds may be combined at molar ratios of 1:1000 to 1000:1, preferably 1:99 to 99:1, preferably 10:90 to 90:10, more preferably 20:80 to 80:20, more preferably 30:70 to 70:30, more preferably 40:60 to 60:40. The particular ratio chosen will depend on the end product desired and/or the method of activation. One practical method to determine which ratio is best to obtain the desired polymer is to start with a 1:1 ratio, measure the desired property in the product produced and adjust the ratio accordingly.

The two metal catalyst compounds and the activator(s) may be supported or unsupported. In some embodiments the first metal catalyst compound may be supported with or without an activator and the second metal catalyst compound may be separately supported with or without an activator. Likewise a metal catalyst compound may be combined with an activator then placed on a support, and thereafter contacted with a solution of the second metal catalyst compound and thereafter introduced into the reactor. In another embodiment both metal catalyst compounds are placed in a liquid solvent or diluent with at least one activator and are introduced into the reactor. In another embodiment the two metal compounds are each combined with an activator in separate liquids and are thereafter mixed in-line on the way to being introduced into the reactor. In another embodiment the a first metal catalyst compound is combined with an activator in solution and a second metal catalyst compound is combined with the solution in-line just prior to entry into the reactor. In another embodiment a first metal compound is contacted with an activator and thereafter placed upon a support and calcined. Thereafter the calcined combination is placed in a slurry (preferably a mineral oil slurry). The slurry is then combined with a liquid carrier containing a second metal catalyst compound and optional activator, and thereafter introduced into the reactor.

Gas Phase Process

Typically in a gas phase oligomerization or polymerization process a continuous cycle is employed where in one part of the cycle of a reactor system, a cycling gas stream, otherwise known as a recycle stream or fluidizing medium, is heated in the reactor by the heat of reaction. This heat is removed from the recycle composition in another part of the cycle by a cooling system external to the reactor. Generally, in a gas fluidized bed process for producing oligomers, a gaseous stream containing one or more monomers is continuously cycled through a fluidized bed in the presence of a catalyst under reactive conditions. The gaseous stream is withdrawn from the fluidized bed and recycled back into the reactor. Simultaneously, product is withdrawn from the reactor and fresh monomer is added to replace the reacted monomer. (See for example U.S. Pat. Nos. 4,543,399, 4,588, 790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70 ° C. to about 95° C.

The productivity of the catalyst or catalyst system in a gas phase system is influenced by the main monomer partial pressure. The preferred mole percent of the main monomer, ethylene or propylene, preferably ethylene, is from about 25 to 90 mole percent and the monomer partial pressure is in the range of from about 75 psia (517 kPa) to about 300 psia (2069 kPa), which are typical conditions in a gas phase process.

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

The catalyst system, the metal catalyst compounds and or the activator may also be introduced into the reactor in solution. In one embodiment a solution of the activated catalyst in an alkane such as pentane, hexane, isopentane or the like is fed into a gas phase reactor.

Slurry Phase Process

A slurry oligomerization or polymerization process generally uses pressures in the range of from about 1 to about 50 atmospheres and even greater and temperatures in the range of 0° C. to about 120° C. In a slurry phase process, a suspension of solid, particulate oligomer or polymer is formed in a liquid diluent medium to which ethylene and comonomers along with catalyst are added. The suspension including diluent is intermittently or continuously removed from the reactor where the volatile components are separated from the product and recycled, optionally after a distillation, to the reactor. Volatile alpha-olefin products are separated from this stream and removed for further processing. The liquid diluent employed in the reaction medium is typically an alkane having from 3 to 7 carbon atoms, preferably a branched alkane. The medium employed should be liquid under the conditions of reaction and relatively inert. When a propane medium is used the process must be operated above the reaction diluent critical temperature and pressure. Preferably, a hexane or an isobutane medium is employed.

In one embodiment, a preferred polymerization technique is referred to as a particle form polymerization, or a slurry process where the temperature is kept below the temperature at which the oligomer goes into solution. Such technique is well known in the art, and described in for instance U.S. Pat. No. 3,248,179 which is fully incorporated herein by reference. The preferred temperature in the particle form process is within the range of about 185° F. (85° C.) to about 230° F. (110° C.). Preferred oligomerization or polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst system as a slurry in isobutane or as a dry free flowing powder is injected regularly to the reactor loop, which is itself filled with circulating slurry of growing oligomer particles in a diluent of isobutane containing monomer and comonomer. Hydrogen, optionally, may be added as a molecular weight control. The reactor is maintained at pressure of about 525 psig to 625 psig (3620 kPa to 4309 kPa) and at a temperature in the range of about 140° F. to about 220° F. (about 60° C. to about 104° C.) depending on the desired product density. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon-free powder is then compounded for use in various applications.

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of ethylene in the reactor liquid medium is in the range of from about 1 to 10 weight percent, preferably from about 2 to about 7 weight percent, more preferably from about 2.5 to about 6 weight percent, most preferably from about 3 to about 6 weight percent.

The catalyst system, the metal catalyst compounds and or the activator may also be introduced into the reactor in solution. In one embodiment a solution of the activated catalyst in an alkane such as pentane, hexane, isopentane or the like is feed into a gas phase reactor.

Solution Process

The oligomerization process is preferably conducted in a liquid. The liquid phase reaction can be undertaken by dissolving catalyst system in a solvent or suspending the catalyst system in a liquid medium. The solvent or liquid medium should be inert to process components and apparatus under process conditions. Examples of solvents are, alkanes, alkenes, cycloalkanes, selected halogenated hydrocarbons, and aromatic hydrocarbons. Specific useful solvents include hexane, iso-pentane, toluene, the alpha-olefins themselves, benzene and mixtures of the foregoing. Solvents which permit phase separation from oligomer product, for example fluorocarbons, are sometimes preferred because product can then be isolated by decantation. Other methods of product separation such as distillation may be utilized.

The oligomerization or cooligomerization process can be run at a temperature in the range of about 0° C. to about 200° C. Preferred temperatures are in the range of about 30° C. to about 140° C. It is suggested that a commercial unit be run in the range of about 60° C. to about 130° C.

Subject process can be run at pressures in the range of about atmospheric pressure to about 5000 psig. Preferred pressures are in the range of about 10 psig to about 2000 psig. These pressures are the pressures at which the ethylene or ethylene/propylene feed is introduced into the reactor, and at which the reactor is maintained. Pressure can influence the performance of the catalyst. Typical catalyst concentrations are in the range of about 0.1 ppm (parts per million) to about 1000 ppm of transition metal. The ppm is based on a million parts by weight of transition metal. A preferred range is about 0.1 ppm to about 100 ppm.

At high reaction rates, the reactions can be ethylene mass-transfer rate limited. At lower catalyst concentrations (1 ppm versus 50 ppm Zr), the catalyst turnover frequency, which is defined as moles of ethylene per moles of transition metal per hour or gram ethylene per gram transition metal per hour, increases. Catalyst activity can be increased (on a per Zr basis) by increasing the molar ratio of cocatalyst, especially alumoxane, to catalyst.

EXAMPLES

Gas chromatographic analyses were performed using a Hewlett-Packard 6890 Plus GC equipped with a ChemStation (version A.06.03) with flame ionization detection. Analyses utilized a J&W DB-1301 column (10 m×180 µm×0.40 µm film thickness) and temperature programmed method ($T_i$=60° C., $t_i$=0.75 min, rate=40° C./min, $T_f$=275° C.; He carrier).

GC-MS analyses were performed using a Hewlett-Packard 6890 GC equipped with a ChemStation (version A.06.03) and model 5973 mass selective detector. Analyses utilized a J&W DB-1301 column (10 m×180 µm×0.40 µm film thickness) and temperature programmed method ($T_i$=100° C., $t_i$=2.00 min, rate=25° C./min, $T_f$=275° C.; He carrier).

Example 1

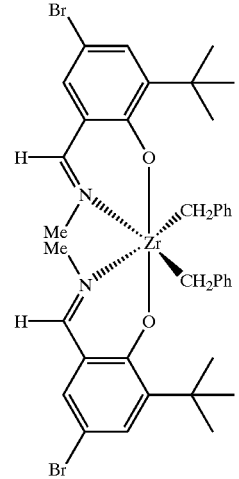

Compound A 3-t-Butyl-5-bromosalicylaldehyde (10.0 g, 38.7 mmol) was dissolved in 50 mL MeOH under nitrogen. The suspension was cooled to 0° C., and 19.4 mL (38.8 mmol) of 2M MeNH$_2$ in MeOH (Aldrich) was added via a dropping funnel. The solution was stirred for 45 min and then concentrated under vacuum to yield a yellow solid (7.86 g) which was dried under vacuum. $^1$H NMR (CDCl$_3$) δ8.37 (q, J=1.5 Hz, 1H, HC=N), 7.42 (d, J=2.5 Hz, 1H, aryl), 7.37 (d, J=2.5 Hz, 1H, aryl), 3.45 (d, J=1.5 Hz, 3H, NMe), 1.41 (s, 9H, t-Bu). The phenol —OH resonance was not observed. Compound A was prepared in situ from reaction of ZrBz$_4$ with 2 equiv of N—Me-3-t-butyl-5-bromosalicylimine in toluene for 5 min.

Slurry oligomerizations were performed under 85 psi (0.6 MPa) ethylene in a 1 L stirred reactor charged with 600 mL hexane, 43 mL hexene and iso-Bu$_3$Al (100 mmol) at 75° C.

Catalyst (Compound A) was activated by slow addition (2 min) of MMAO to a toluene solution of catalyst. Oligomerizations were performed for 30 min. MMAO is modified methylalumoxane (type 3 in hexane) commercially available from Akzo Chemicals, Inc. under the trade name Modified Methylalumoxane type 3A, covered under U.S. Pat. No. 5,041,584.

Rapid gas uptake was observed upon exposure to ethylene. The reaction was terminated after 30 min, and 79 g of a white, waxy solid was obtained after evaporation of hexane under vacuum. The high activity of this catalyst (372 kg product/mmol Zr·hr·100 psi $C_2H_4$) is comparable to Phenoxide catalysts which produce high molecular weight polyethylene. (The activity reported is based on the mass of recovered material after drying under vacuum. Correction for loss of volatile oligomers (butene, hexene, octene) would result in a higher actual oligomerization activity.) The waxy nature of this solid, as well as its solubility in toluene, was indicative of the low molecular weight of this material. GC-MS analysis indicated that the product comprised a mixture of linear α-olefins in the $C_{10}$–$C_{40}$ range (FIG. 1). Higher molecular weight products, if present, were not eluted from the column. No evidence for odd-carbon products was obtained, indicating that chain transfer to aluminum did not occur.

Figure 2:
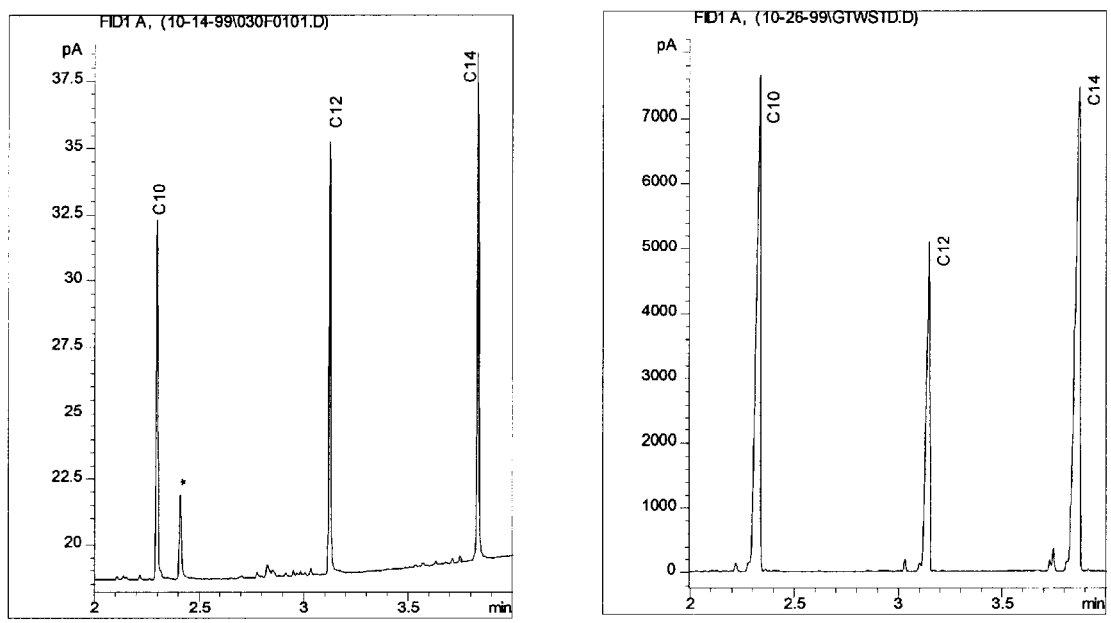
FIG. 2 is a comparison of purity of $C_{10}$–$C_{14}$ products from Example 1 (left) with commercial samples of 1-decene (94%), 1-dodecene (95%) and 1-tetradecene (92%) obtained from Aldrich (right). Peak marked with * is due to a solvent impurity.
Figure 3:
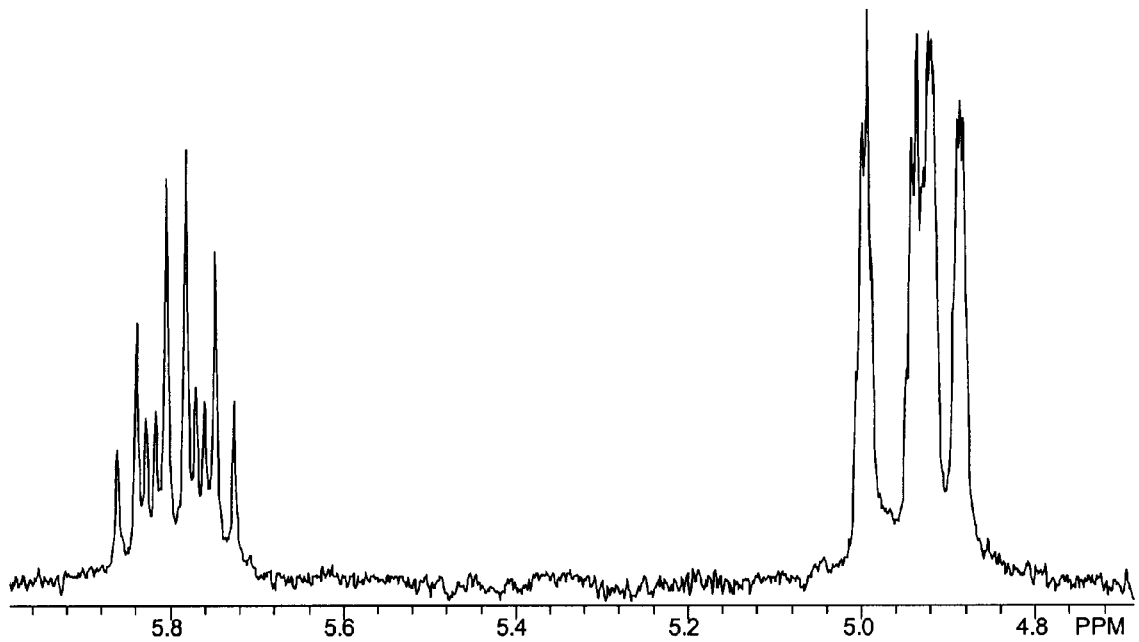
FIG. 3 shows the olefinic region of $^1$H NMR spectrum of ethylene oligomers produced in Example 1. No signals near δ5.4 due to internal olefinic isomers were detectable.

The α-olefins produced by this catalyst system were found to be highly linear with no evidence of internal olefin isomers. Comparison of the $C_{10}$, $C_{12}$ and $C_{14}$ α-olefin fractions with commercial samples (Aldrich) indicated the oligomeric products formed by the Zr-salicylimine catalyst were of higher purity (FIG. 2). No peaks due to olefin isomers were detectable by GC or GC-MS analyses which indicated a linear purity of ≧99%. The $^1$H NMR spectrum of this oligomeric mixture in $CDCl_3$ (FIG. 3) was consistent with the high isomeric purity observed by GC. Resonances due to terminal, vinylic protons at δ5.8 ($H_2C$=C<u>H</u>R) and 4.9 (<u>H</u>$_2$C=CHR) were observed with no detectable signals near δ5.4 due to internal isomers.

Example 2

The effect of reaction conditions on the Schulz-Flory α value of Compound A was investigated. Neither decreased ethylene pressure nor increased temperature led to observable changes in α. When the ethylene oligomerization was conducted at 105° C. and 48 psig ethylene, no change in α was observed by GC analysis.

All documents described herein are incorporated by reference herein, including any priority documents and/or testing procedures. As is apparent form the foregoing general description and the specific embodiments, while forms of the invention have been illustrated and described, various modifications can be made without departing from the spirit and scope of the invention. Accordingly it is not intended that the invention be limited thereby.

We claim:

1. A method to oligomerize ethylene comprising combining ethylene with a catalyst system comprising an activator and one or more phenoxide metal compounds represented by the formula:

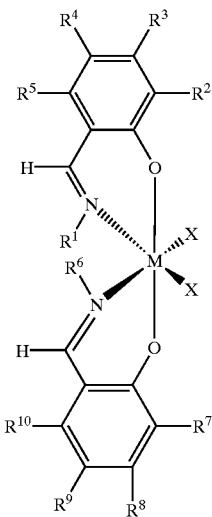

wherein
$R^3$, $R^4$, $R^5$, $R^8$, $R^9$ and $R^{10}$ are each independently selected from hydrogen, a halogen, a heteroatom containing group or a $C_1$ to $C_{100}$ group, provided that at least one of these groups has a Hammett $\sigma_p$ value (Hansch, et al Chem. Rev. 1991, 91, 165) greater than 0.20;

$R^2$ and $R^7$ are each independently selected from alkyl, aryl or silyl groups;

$R^1$ and $R^6$ may each independently selected from an alkyl group, an aryl group, an alkoxy group, or an amino group;

N is nitrogen;

H is hydrogen;

O is oxygen;

M is a group 4 transition metal; and each X is independently an anionic ligand or a dianionic ligand.

2. The method of claim 1 wherein the activator is an aluminum alkyl, an alumoxane, a modified alumoxane, a borane, a borate or a non-coordinating anion, or a mixture thereof.

3. The method of claim 1 wherein M is Zr.

4. The method of claim 1 wherein either the phenoxide metal compound or the activator or both are placed on a support.

5. The method of claim 1 wherein the activator is one or more of alumoxane, tris(2,2',2"-nonafluorobiphenyl) fluoroaluminate, triphenyl boron, triethyl boron, tri-n-butyl ammonium tetraethylborate, triaryl borane, tri(n-butyl) ammonium tetrakis pentafluorophenyl) boron or a trisperfluorophenyl boron, or diethylaluminum chloride.

6. The method of claim 1 wherein each X independently is a halide, alkyl, aryl, hydride, carboxylate, alkoxide or amide, dialkoxide or diamide.

7. The method of claim 1 wherein $R^3$, $R^4$, $R^5$, $R^8$, $R^9$ and $R^{10}$ are each independently selected from Br, Cl, —$C_6Cl_5$, —$C_6F_5$, —$OCF_3$, —CHO, —$CF_3$ or —$NO_2$.

8. The method of claim 1 wherein $R^2$ and $R^7$ are each independently selected from t-butyl, t-amyl, —$CMe_2Ph$, —$CMePh_2$, —$CPh_3$, —$SiMe_3$, —$SiEt_3$, —$SiMe_2tBu$, —$SiMe_2Ph$, —$SiPh_3$, α-naphthyl, phenanthrenyl or anthracenyl groups.

9. The method of claim 1 wherein $R^1$ and $R^6$ may each independently selected from methyl, ethyl, propyl or cyclopropyl or fluorinated alkyl groups, preferably —CH$_2$CF$_3$ or —CH$_2$CF$_2$CF$_3$.

10. The method of claim 1 wherein each X is independently a halogen.

11. The method of claim 1 wherein either the phenoxide metal compound or the activator or the reaction product thereof are placed on a support.

12. The method of claim 1 wherein the transition metal compound and the activator are combined in ratios of about 1000:1 to about 0.5:1.

13. The method of claim 1 wherein the activator is an alkyl aluminum compound and the phenoxide metal compound and the alkyl aluminum compound are combined in ratios of about 0.5:1 to about 10:1.

14. The method of claim 1 the process is a gas phase process, a slurry phase process, a slurry phase solution process, or high pressure process.

* * * * *

UNITED STATES PATENT AND TRADEMARK OFFICE
CERTIFICATE OF CORRECTION

PATENT NO. : 6,531,555 B2
DATED : March 11, 2003
INVENTOR(S) : Whiteker

It is certified that error appears in the above-identified patent and that said Letters Patent is hereby corrected as shown below:

Title page,
Item [73], Assignee, "Univation Technologies, LLP, Houston, Texas (US)" should be deleted and -- Univation Technologies, LLC, Houston, Texas (US) -- inserted therefore.
Item [57], ABSTRACT, the formula 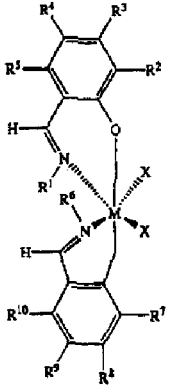 should be Deleted, and -- 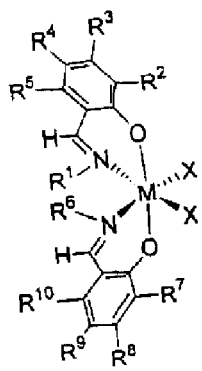 -- inserted therefore.

Signed and Sealed this

Twenty-second Day of March, 2005

JON W. DUDAS
*Director of the United States Patent and Trademark Office*